(12) United States Patent
Hase et al.

(10) Patent No.: US 8,685,733 B2
(45) Date of Patent: Apr. 1, 2014

(54) CELL SHEET HAVING GOOD DIMENSIONAL STABILITY, METHOD FOR PRODUCTION THEREOF, AND CELL CULTURE CARRIER FOR USE IN THE METHOD

(75) Inventors: Masahiko Hase, Shinjuku-ku (JP); Hideshi Hattori, Shinjuku-ku (JP)

(73) Assignee: Dai Nippon Printing Co., Ltd., Tokyo (JP)

( * ) Notice: Subject to any disclaimer, the term of this patent is extended or adjusted under 35 U.S.C. 154(b) by 186 days.

(21) Appl. No.: 12/599,675

(22) PCT Filed: May 9, 2008

(86) PCT No.: PCT/JP2008/058985
§ 371 (c)(1),
(2), (4) Date: Nov. 10, 2009

(87) PCT Pub. No.: WO2008/143149
PCT Pub. Date: Nov. 27, 2008

(65) Prior Publication Data
US 2011/0151565 A1 Jun. 23, 2011

(30) Foreign Application Priority Data
May 11, 2007 (JP) ................................. 2007-126677

(51) Int. Cl.
*C12N 5/00* (2006.01)
(52) U.S. Cl.
USPC ........................................................ 435/401
(58) Field of Classification Search
USPC .................. 435/395–397, 401, 402
See application file for complete search history.

(56) References Cited

U.S. PATENT DOCUMENTS

| 2003/0228693 | A1 | 12/2003 | Tsuzuki et al. |
| 2004/0009590 | A1* | 1/2004 | Tan et al. ........................ 435/366 |
| 2005/0181973 | A1* | 8/2005 | Genove et al. ..................... 514/2 |

(Continued)

FOREIGN PATENT DOCUMENTS

| EP | 1748064 A1 | 1/2007 |
| EP | 1 840 207 A1 | 10/2007 |

(Continued)

OTHER PUBLICATIONS

Kotch et al., Self-assembly of synthetic collagen trip[le helices, 2006, PNAS 103(9): 3028-3033.*

(Continued)

*Primary Examiner* — Jon P Weber
*Assistant Examiner* — Robert Yamasaki
(74) *Attorney, Agent, or Firm* — Sughrue Mion, PLLC

(57) ABSTRACT

It is an object of the present invention to provide a cell culture carrier for producing a cell sheet that can be readily detached from a cell culture carrier and is inhibited from contracting after being detached.

The cell culture carrier 1 of the present invention comprises: a support-held culture membrane 4 comprising an organic thin film 2 having cell adhesion properties and biodegradability and a frame-like support 3 fixed on the periphery of the organic thin film for maintaining the dimensions of the organic thin film; and a base substrate 6 having a surface 5 with a static water contact angle of 45° or less, wherein the support-held culture membrane 4 is detachably placed on the surface 5 of the base substrate.

10 Claims, 15 Drawing Sheets
(8 of 15 Drawing Sheet(s) Filed in Color)

(56) References Cited

U.S. PATENT DOCUMENTS

| | | |
|---|---|---|
| 2006/0153815 A1* | 7/2006 | Seyda et al. .................. 424/93.7 |
| 2006/0177927 A1* | 8/2006 | Tan et al. ...................... 435/366 |
| 2007/0015272 A1 | 1/2007 | Ogura et al. |
| 2007/0092493 A1* | 4/2007 | Sung et al. .................. 424/93.7 |
| 2007/0274968 A1 | 11/2007 | Hattori et al. |
| 2008/0226692 A1 | 9/2008 | Sato et al. |

FOREIGN PATENT DOCUMENTS

| | | |
|---|---|---|
| JP | 08-224076 A | 9/1996 |
| JP | 2887737 A | 4/1999 |
| JP | 2004-329045 A | 11/2004 |
| JP | 2006-191809 A | 7/2006 |
| JP | 2006-217878 A | 8/2006 |
| JP | 2007-024576 A | 2/2007 |
| WO | 03/053217 A2 | 7/2003 |
| WO | 2006/075597 A1 | 7/2006 |
| WO | 2006/093151 A1 | 9/2006 |

OTHER PUBLICATIONS

Co et al., Biocompatible Micropatterning of Two Different Cell Types, 2005, J. Am. Chem. Soc. 127: 1598-1599.*

Anderson et al., Amniotic membrane transplantation for partial limbal stem cell deficiency, 2001, British Journal of Ophthalmology 85:567-575.*

European Search Report dated Apr. 28, 2010 for European Patent Application No. 08752839.4-401.

Office Action issued on Aug. 21, 2012, in corresponding Japanese Patent Application No. 2009-515198.

Extended Search Report issued in corresponding European Patent Application No. 13165622.5 on Jul. 12, 2013.

* cited by examiner (a)

(b)

(a)

(b)

(c)

(a)

(b)

(c)

CELL SHEET HAVING GOOD DIMENSIONAL STABILITY, METHOD FOR PRODUCTION THEREOF, AND CELL CULTURE CARRIER FOR USE IN THE METHOD

TECHNICAL FIELD

The present invention relates to a cell sheet having good dimensional stability and being inhibited from contracting, a method for production of such cell sheet, and a cell culture carrier for use in such method, which can be used in fields related to cell tissue-based pharmaceutical products such as the fields of medical treatment (including regenerative medicine), drug discovery, diagnosis, and medical examination.

BACKGROUND ART

The technology for producing cell sheets is important in the field of tissue engineering; however, it has some drawbacks.

First, it is difficult to detach a cell sheet cultured on a cell culture substrate from the substrate, which is problematic. In addition, even if such cell sheet can be detached from the substrate, the cell sheet contracts after detachment. In such case, it is difficult to handle the obtained cell sheet in the subsequent steps, which is also problematic.

For example, Patent Document 1 discloses a technique comprising providing a temperature responsive polymer to the surface of a cell culture base substrate in order to facilitate the detachment of a cell sheet, culturing a cell sheet thereon, and changing the temperature so as to allow the detachment of the cell sheet. However, the technology is not applicable to some cell species that are difficult to detach. Further, the problem of contraction of a detached cell sheet has not been solved by the above technique. Furthermore, it is difficult to produce a thick cell sheet by the above technique, which is also problematic.

Patent Document 2 discloses a technique for coating a substrate surface with fibrin glue in order to facilitate the detachment of a cell sheet. Patent Document 2 describes that fibrin glue is degraded by an enzyme contained in cells and disappears such that cells binding to each other and forming a cell sheet become suspended, facilitating the detachment of the cell sheet. However, in Patent Document 2, a scraper is used to detach the cell sheet. Therefore, it cannot be said that a sufficient degree of detachability has been achieved in the above case. Further, it is thought that some cell species cannot cause sufficient degradation of fibrin glue. In addition, the problem of contraction of a detached cell sheet has not been solved yet.

In addition to be above, techniques for facilitating the detachment of a cell sheet by controlling adhesiveness between a cell sheet and a culture substrate have been disclosed (see Patent Documents 3 to 6, etc). However, each one of the above techniques is not applicable for some cell species. In addition, the problem of cell sheet contraction cannot be solved by the above techniques.

Further, there are advanced techniques whereby a multilayer cell sheet can be formed. In the field of tissue engineering, techniques for regenerating thin tissues such as skin tissue and tissues with low cell content such as cartilage tissue have already been used in practice. In addition, many therapeutic methods comprising injecting therapeutically effective cells into lesions are being examined in clinical trials. However, tissue engineering technology has not been established for tissues with higher cell contents (with many examples of such tissues existing). In particular, in order to artificially produce tissues with high oxygen demand (tissues containing blood vessel networks) and tissues comprising parenchymal cells such as heart tissue and liver tissue, it is necessary to adjust the cell sheet thickness to at least 200 μm. However, if usual cell sheets are laminated to the above or a greater thickness, it becomes impossible to supply oxygen in a sufficient amount to cells contained inside the obtained laminate, resulting in necrosis. This is problematic.

Hitherto, in order to supply oxygen to cells, many techniques for forming a cell tissue by seeding cells on a porous scaffold (carrier) comprising, for example, a bioabsorbable material have been examined. However, in the cases of such techniques, it is difficult to achieve uniform distribution of cells inside a scaffold. In addition, a transplanted tissue tends to be fibrosed, which is problematic.

Further, when a multilayer cell sheet is produced, such cell sheet is more likely to contract than single-layer cell sheets, which is also problematic.

Meanwhile, Patent Documents 7 and 8 disclose techniques for culturing cells on a vitrified hydrogel thin film having improved shape retention. Hydrogel thin films comprising collagen and the like described in Patent Documents 7 and 8 are physically strong. Therefore, it is thought that cell sheets cultured on such thin films are unlikely to contract. However, in the above cases, a very thick hydrogel layer is used. Accordingly, even if it is possible to laminate a plurality of cell layers comprising hydrogel layers obtained in Patent Document 7 or 8, an inter-cell-layer network is unlikely to be formed because of large gaps between overlapping cell layers. In addition, it is difficult to obtain inter-cell-layer paracrine interaction that is induced by diffusion of liquid factors or the like. Consequently, the above techniques are not appropriate for production of regenerative tissue.

Patent Document 1: WO2002/008387
Patent Document 2: WO2005/028638
Patent Document 3: JP Patent Publication (Kokai) No. 2006-346292 A
Patent Document 4: JP Patent Publication (Kokai) No. 2006-94799 A
Patent Document 5: JP Patent Publication (Kokai) No. 2005-261292 A
Patent Document 6: JP Patent Publication (Kokai) No. 2006-296896 A
Patent Document 7: WO2005/014774
Patent Document 8: JP Patent Publication (Kokai) No. 8-228768 A (1996)

DISCLOSURE OF THE INVENTION

As described above, no satisfactory techniques whereby cell sheets can be readily detached from cell culture carriers upon cell sheet production while contraction of cell sheets can be inhibited have been established. In addition, no cell sheets that can be appropriately multilayered have been provided.

It is an object of the present invention to solve the above problems.

The present invention comprises the following inventions.
(1) A cell culture carrier, which comprises: a support-held culture membrane comprising an organic thin film having cell adhesion properties and biodegradability and a frame-like support fixed on the periphery of the organic thin film for maintaining the dimensions of the organic thin film; and a base substrate having a surface with a static water contact angle of 45° or less, wherein the support-held culture membrane is detachably placed on the surface of the base substrate.

(2) The cell culture carrier according to (1), wherein the surface of the base substrate has cell adhesion inhibitory properties.

(3) The cell culture carrier according to (1) or (2), wherein the organic thin film is a biologically-derived material.

(4) The cell culture carrier according to (1) or (2), wherein the organic thin film is formed with an artificially synthesized biomimetic material.

(5) The cell culture carrier according to any one of (1) to (4), wherein the organic thin film is formed with a high-molecular compound and the dry weight per unit area of the high-molecular compound is 5 to 100 µg/cm$^2$.

(6) The cell culture carrier according to any one of (1) to (5), wherein the organic thin film is subjected to patterning.

(7) A method for producing a support-held cell sheet, comprising culturing cells on the organic thin film of the cell culture carrier according to any one of (1) to (6) so as to form a sheet-type cell layer and detaching the cell layer with the support-held culture membrane from the base substrate, thereby obtaining a support-held cell sheet comprising the support-held culture membrane and the cell layer.

(8) A support-held cell sheet produced by the method according to (7).

(9) An organic-thin-film-covered support-held cell sheet, which is obtained by covering the surface of the support-held cell sheet according to (8), the surface having the cell layer formed thereon, with an organic thin film having cell adhesion properties and biodegradability.

(10) A multilayer support-held cell sheet, which is obtained by laminating a plurality of support-held cell sheets produced by the method according to (7).

(11) An organic-thin-film-covered multilayer support-held cell sheet, which is obtained by covering the surface of the multilayer support-held cell sheet according to (10), the surface having the cell layer formed thereon, with an organic thin film having cell adhesion properties and biodegradability.

(12) A method for producing a contraction-inhibited cell sheet, comprising: laminating a biodegradable sheet having sufficient strength and cell adhesion properties on the support-held cell sheet according to (8), the organic thin film-covered support-held cell sheet according to (9), the multilayer support-held cell sheet according to (10), or the organic thin film-covered multilayer support-held cell sheet according to (11); allowing the sheets to adhere to each other; and then removing the support therefrom.

(13) A contraction-inhibited cell sheet, which is produced by the method according to (12).

This description includes part or all of the contents as disclosed in the description and/or drawings of Japanese Patent Application No. 2007-126677, which is a priority document of the present application.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 (b) is an A-A' cross section of the cell culture carrier of the present invention shown in FIG. 1 (a).

In FIG. 7, (1) and (2) denote a cell nucleus and a collagen thin film, respectively.

EXPLANATION OF REFERENCE NUMERALS

Figure 1:
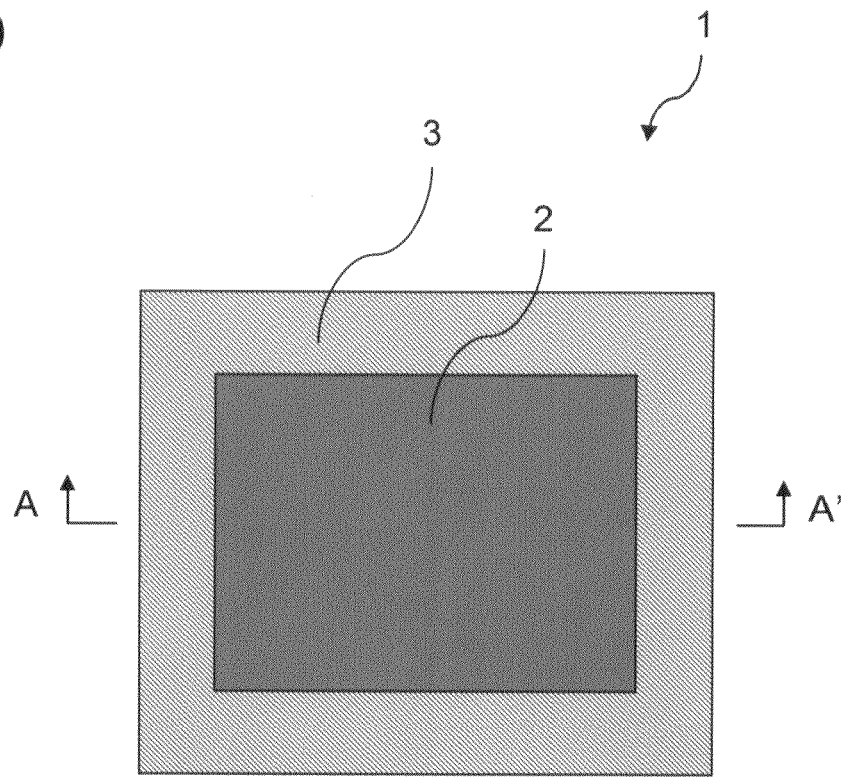
FIG. 1 (a) is an overhead view of the cell culture carrier of the present invention.
Figure 1:
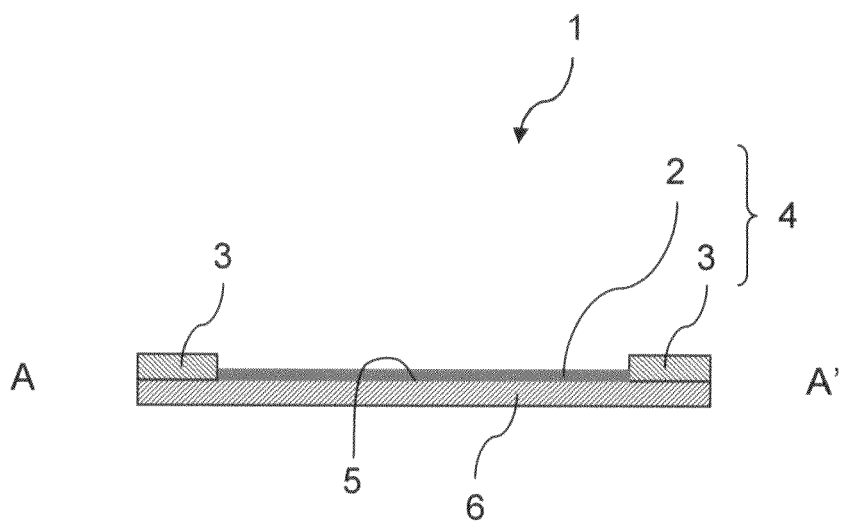

1: Cell culture carrier
2: Organic thin film
3: Support
4: Support-held culture membrane
5: Surface with a static water contact angle of 45° or less
6: Base substrate
7: Sheet-type cell layer
8: Support-held cell sheet
9: Multilayer support-held cell sheet
10: Biodegradable sheet
11: Contraction-inhibited cell sheet
12: Organic-thin-film-covered support-held cell sheet
13: Organic-thin-film-covered multilayer support-held cell sheet

BEST MODE FOR CARRYING OUT THE INVENTION

Cell Culture Carrier Structure

The structure of the cell culture carrier of the present invention is described with reference to FIG. 1. FIG. 1 (a) is an overhead view of the cell culture carrier. FIG. 1 (b) is an A-A' cross section of the cell culture carrier. A cell culture carrier 1 comprises: a support-held culture membrane 4 comprising an organic thin film 2 having cell adhesion properties and biodegradability and a frame-like support 3 fixed on the periphery of the organic thin film 2 for maintaining the dimensions of the organic thin film 2; and a base substrate 6 having a surface 5 with a static water contact angle of 45° or less, in which the support-held culture membrane 4 is provided to the surface 5 of the base substrate 6 in a detachable manner.

(Method for Using a Cell Culture Carrier)

Figure 2:
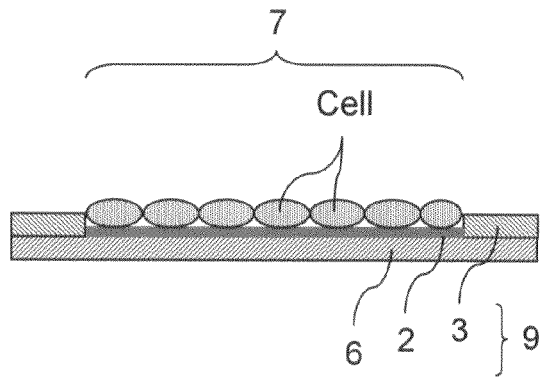
FIG. 2 (a) to (c) schematically show a method for using a cell culture carrier.
Figure 2:
Figure 2:
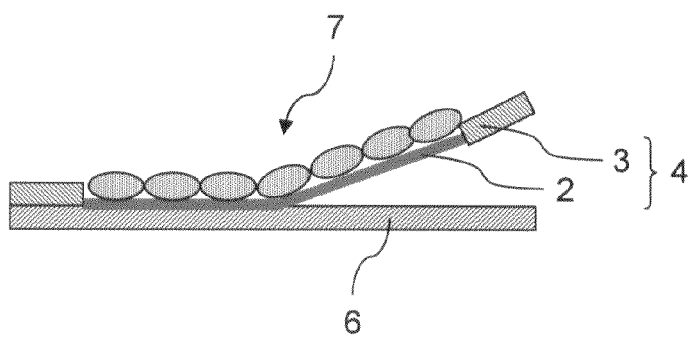
Figure 2:
Figure 2:
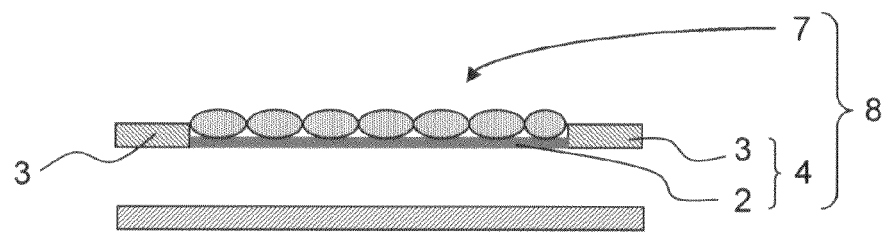

A method for using the cell culture carrier 1 is described with reference to FIG. 2 (a) to (c). First, as shown in FIG. 2 (a), a sheet-type cell layer 7 is formed by culturing desired cells on an organic thin film 2. Next, the cell layer 7 is detached with a support-held culture membrane 4 from a base substrate 6 (FIG. 2 (b)) such that a support-held cell sheet 8 comprising the support-held culture membrane 4 and the cell layer 7 formed on the membrane 4 is obtained (FIG. 2 (c)).

Figure 3:
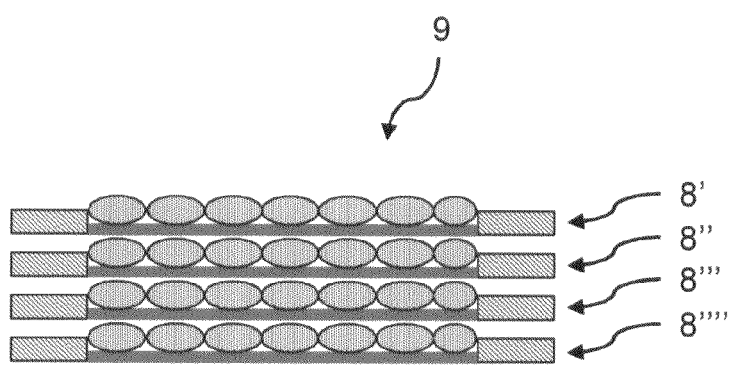
FIG. 3 shows a multilayer support-held cell sheet 9 obtained by laminating a plurality of support-held cell sheets 8.
Figure 14:
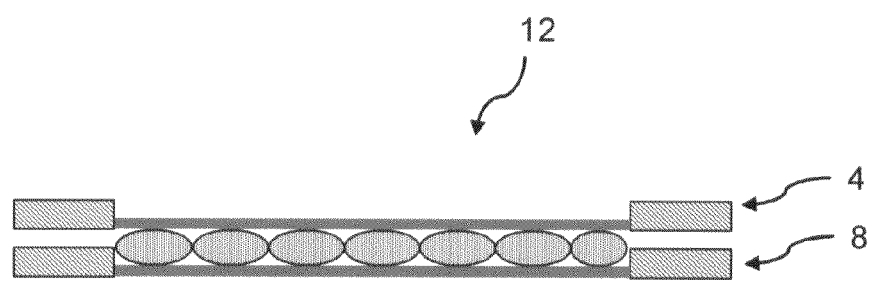
FIG. 14 shows an organic-thin-film-covered support-held cell sheet 12 obtained by covering the surface of a support-held cell sheet 8, the surface having a cell layer formed thereon, with a organic thin film 2 of a support-held culture membrane 4.
Figure 15:
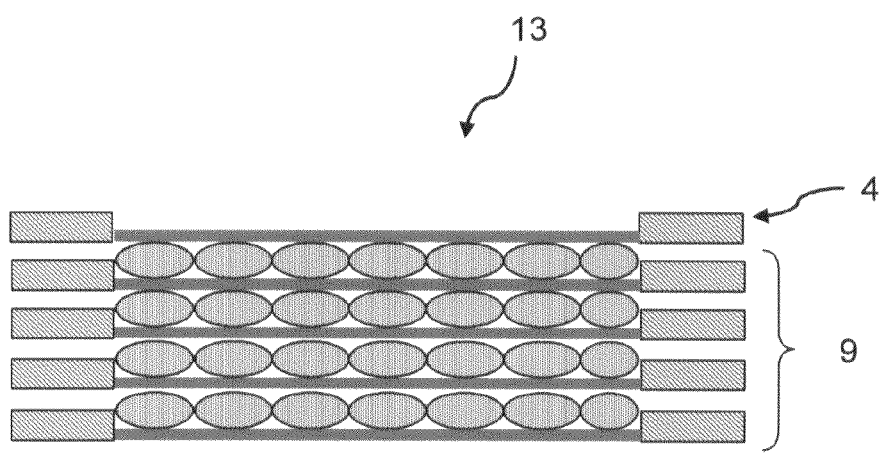
FIG. 15 shows an organic-thin-film-covered multilayer support-held cell sheet 13 obtained by covering the surface of a multilayer support-held cell sheet 9, the surface having a cell layer formed thereon, with a organic thin film 2 of a support-held culture membrane 4.

For instance, as shown in FIG. 3, a plurality of support-held cell sheets 8 can be laminated such that a multilayer support-held cell sheet 9 is obtained. The periphery of the thus produced support-held cell sheet 8 or multilayer support-held cell sheet 9 is supported with a support 3. Therefore, even if the cell sheet is detached from a base substrate 6, it does not contract, and thus it may be readily handled. The support 3 can be separated from the support-held cell sheet 8 or multilayer support-held cell sheet 9 by cutting following transplantation to a living body. In addition, if the support 3 is formed with a biodegradable material, there is no need to separate the support 3 by cutting after transplantation. Individual support-held cell sheets used for production of a multilayer support-held cell sheet may be cell sheets comprising homogeneous cells or cell sheets comprising heterogeneous cells. The surface of the support-held cell sheet 8 or multilayer support-held cell sheet 9, the surface having a cell layer formed thereon, may be covered with an organic thin film having cell adhesion properties and biodegradability. An organic thin film used for covering may be identical to an organic thin film constituting a support-held culture membrane. In addition, as the organic thin film used for covering, a support-held culture membrane shown in FIG. 1 or the like, which has a periphery supported by a frame-like support, is preferably used. FIG. 14 shows an example of an organic thin film-covered support-held cell sheet 12 obtained by covering the surface of a support-held cell sheet 8, the surface having a cell layer formed thereon, with an organic thin film 2 of a support-held culture membrane 4. FIG. 15 shows an example of an organic-thin-film-covered multilayer support-held cell sheet 13 obtained by covering the surface of a multilayer support-held cell sheet 9, the surface having a cell layer formed thereon, with a organic thin film 2 of a support-held culture membrane 4.

Figure 4:
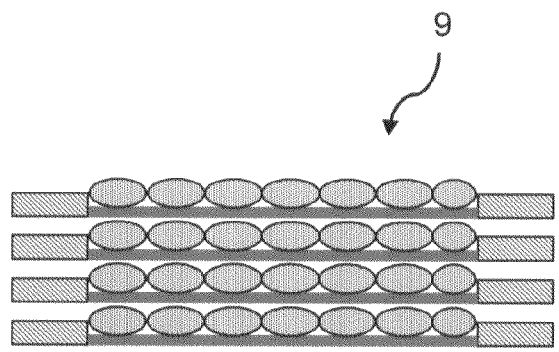
FIG. 4 schematically shows a method for producing a contraction-inhibited cell sheet.
Figure 4:
Figure 4:
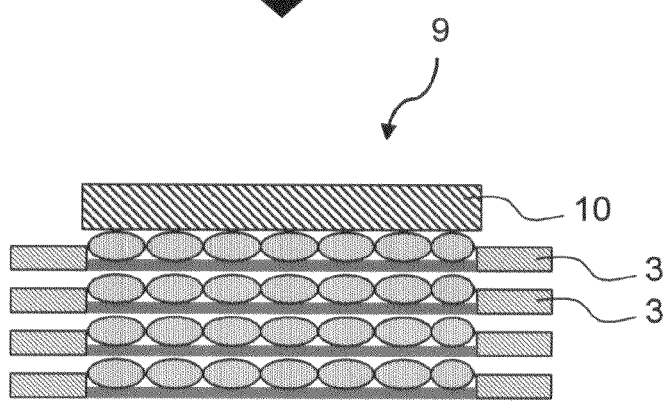
Figure 4:
Figure 4:
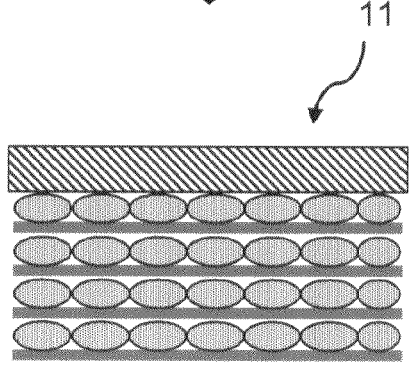

In addition, as shown in FIG. 4, it is also possible to further process the support-held cell sheet 8 or multilayer support-held cell sheet 9 into a contraction-inhibited cell sheet 11. Specifically, a biodegradable sheet 10 having sufficient strength and cell adhesion properties is laminated on a multilayer support-held cell sheet 9 (FIG. 4 (b)). Both sheets are maintained in a laminated position for a certain period of time for adhesion. Subsequently, the support 3 is removed therefrom such that a contraction-inhibited cell sheet 11 can be obtained (FIG. 4 (c)). FIG. 4 shows an example involving the use of a multilayer support-held cell sheet 9. Alternatively, it is possible to process a single-layer support-held cell sheet to result in a contraction-inhibited cell sheet in a similar manner. In addition, a plurality of biodegradable sheets can be used.

Further, the contraction-inhibited cell sheet of the present invention includes a sheet obtained by laminating a plurality of contraction-inhibited cell sheets.

Figure 5:
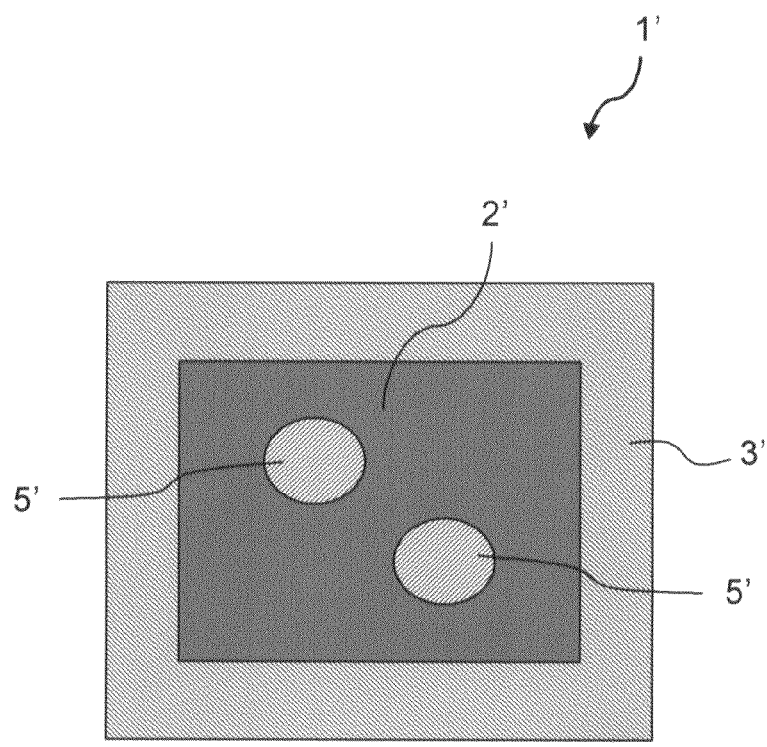
FIG. 5 is an overhead view of a cell culture carrier having a patterned organic thin film.

In addition, an organic thin film may be subjected to patterning. For instance, in FIG. 5, an organic thin film 2' is subjected to patterning such that it has two openings for exposure of a base surface 5' of a material 6'. The surface 5' of the base substrate 6' has a static water contact angle of 45° or less so as to be hydrophilic so that cells do not adhere thereto, allowing formation of a cell layer in accordance with the pattern on the organic thin film 2' (not shown). As described above, a support-held cell sheet produced with the use of the cell culture carrier 1' having a patterned organic thin film 2' has pores at desired sites. A multilayer cell sheet obtained by laminating a plurality of such support-held cell sheets has pores at desired sites and therefore oxygen and the like can be supplied to the internal portion of such thick cell sheet. Therefore, it is expected that problems of cell necrosis and the like can be solved.

Next, the configuration of the present invention is described in detail below.

(Organic Thin Film)

The organic thin film used herein is not particularly limited as long as it has cell adhesion properties and biodegradability. However, preferably, it comprises a biologically-derived material. Specific examples of materials include gels formed with high-molecular compounds such as various types of collagens, peptide hydrogel, laminin, chondronectin, glycosaminoglycan, hyaluronic acid, proteoglycan, extracellular matrix component proteins other than the above examples, a basement membrane component reconstructed with a mouse EHS tumor extract (product name: Matrigel), gelatine, agarose, oligonucleic acid, and polynucleic acid.

In addition, in consideration of possible limitation of the therapeutic use of animal-derived and biologically-derived materials in the future, artificially synthesized biomimetic materials other than biological extracts are also preferable. Examples of such materials include various types of artificial peptides and derivatives thereof, artificial oligopeptides and derivatives thereof, artificial polypeptides and derivatives thereof, and artificial polysaccharides and derivatives thereof.

For instance, the thickness of an organic thin film is determined in a manner such that the dry weight of a high-molecular compound per unit area is 5 to 100 $\mu g/cm^2$, and preferably 20 to 40 $\mu g/cm^2$. As described above, organic thin films are very thin. Therefore, it is thought that an inter-cell-layer network is likely to be formed by laminating cell sheets produced in the present invention. In addition, it can be expected that an inter-cell-layer paracrine interaction can be obtained. The support-held cell sheet obtained by the present invention has a support fixed on the periphery thereof, allowing prevention of dimensional changes in an organic thin film caused by contraction of a cell sheet or the like. Therefore, such cell sheet can be readily handled even with the use of such a thin organic thin film by which advantageous effects can be expected. In addition, adhesiveness between such cell sheet and a base substrate having a surface with a static water contact angle of 45° or less that is used in the present invention is adequately weak (but strong enough to prevent spontaneous detachment therebetween under ordinary cell culture conditions). Accordingly, even when an organic thin film with a very small thickness is used, it can be detached from the base substrate surface without damage.

An organic thin film may be formed into a desired pattern via patterning. Examples of a patterning method include: a method comprising forming an organic thin film and etching specific regions on the organic thin film with a dissolving agent; a method comprising directly applying a liquid organic substance in a pattern to a substrate by ink jet printing or the like, followed by drying; a method comprising forming an organic thin film on a substrate having a surface to which a resist has adhered in a pattern and removing the resist; and a method comprising applying a liquid organic substance to a substrate via a punched mask, followed by drying.

(Support)

A frame-like support is fixed on the periphery of the organic thin film for maintaining the dimensions of the organic thin film. A support material is not particularly limited as long as it can bind to the organic thin film. However, examples thereof include polymers such as polyimide, polyester, and nylon, and biodegradable polymers such as polylactic acid. The support thickness is not particularly limited as long as a strength that can withstand contraction in the width direction of a cell layer can be secured. However, the thickness is preferably less than the thickness of a cell layer to be cultured. Specifically preferably, it is 1 to 20 μm. In addition, a biodegradable support is preferably used because it can be directly transplanted.

(Support-Held Culture Membrane)

In the present invention, the entirety of the organic thin film having the periphery on which the support has been fixed is referred to as a "support-held culture membrane." A support-held culture membrane is provided to a base substrate in a detachable manner. After cell culture on the organic thin film, it is possible to detach the membrane from the base substrate by holding the support with a pair of tweezers or the like.

(Base Substrate)

The base substrate has a surface with a static water contact angle of 45° or less. The support-held culture membrane is in contact with the surface. In general, the base substrate surface with the above static water contact angle tends to have cell adhesion inhibitory properties. In the case of the aforementioned organic thin film with a very low thickness, if the base substrate surface has cell adhesion properties, it is difficult to detach the support-held cell sheet from the base substrate. This is because cultured cells adhere to the base substrate surface via the organic thin film or because an enzyme contained in cells degrades the organic thin film such that cells adhere to the base substrate surface. However, if the base substrate surface has cell adhesion inhibitory properties, such problems can be solved. Even if the organic thin film has a very low thickness as described above, the support-held cell sheet can be readily detached from the base substrate. Such cell adhesion inhibitory surface can be obtained by forming a coating membrane of an organic compound having carbon-oxygen bonds on the surface of a base substrate.

Preferably, a material used for a base substrate has a surface on which a coating membrane of an organic compound having carbon-oxygen bonds can be formed. Specific examples of such a material include: inorganic materials such as metals, glass, ceramic, and silicon; and organic materials represented by elastomers and plastics (e.g., polyester resin, polyethylene resin, polypropylene resin, ABS resin, nylon, acrylic resin, fluorine resin, polycarbonate resin, polyurethane resin, methylpentene resin, phenol resin, melamine resin, epoxy resin, and vinyl chloride resin). The shape of the substrate is not limited. For instance, such substrate can be formed into a flat plate, a flat membrane, a film, a porous membrane, and the like, which have flat shapes, or it can be formed into a cylinder, a stamp, a multiwell plate, a microchannel, and the like, which have steric shapes. When a film is used, the thickness thereof is not particularly limited. However, it is generally 0.1 to 1000 μm, preferably 1 to 500 μm, and more preferably 10 to 200 μm.

The cell adhesion inhibitory surface can be formed with a hydrophilic membrane having a static water contact angle of 45° or less and comprising an organic compound having carbon-oxygen bonds.

In the present invention, the term "carbon-oxygen bond" refers to a bond formed between a carbon atom and an oxygen atom, which may be a single bond or double bond. Examples of a carbon-oxygen bond include a C—O bond, a C(=O)—O bond, and a C=O bond.

Examples of main materials for a hydrophilic membrane include hydrophilic organic compounds such as water-soluble polymers, water-soluble oligomers, water-soluble organic compounds, surfactant substances, and amphipathic substances. These materials are physically or chemically crosslinked to each other and the resultant physically or chemically binds to a base substrate such that a hydrophilic membrane can be formed.

Specific examples of water-soluble polymer materials include polyalkylene glycol and derivatives thereof, polyacrylic acid and derivatives thereof, polymethacrylic acid and derivatives thereof, polyacrylamide and derivatives thereof, polyvinylalcohol and derivatives thereof, zwitterionic polymers, and polysaccharides. In terms of the molecular shape, linear polymers, branched polymers, dendrimers, and the like can be used. Specific examples of the above polymers include, but are not limited to, polyethylene glycol, copolymers of polyethylene glycol and polypropylene glycol (e.g., Pluronic F108 and Pluronic F127), poly(N-isopropylacrylamide), poly(N-vinyl-2-pyrrolidone), poly(2-hydroxyethyl methacrylate), poly(methacryloyloxyethylphosphorylcholine), copolymers of methacryloyloxyethylphosphorylcholine and acrylic monomers, dextran, and heparin.

Specific examples of water-soluble oligomer materials and water-soluble low-molecular compounds include alkylene glycol oligomers and derivatives thereof, acrylic acid oligomers and derivatives thereof, methacrylic acid oligomers and derivatives thereof, acrylamide oligomers and derivatives thereof, saponified products of vinyl acetate oligomers and derivatives thereof, oligomers comprising zwitterionic monomers and derivatives thereof, acrylic acid and derivatives thereof, methacrylic acid and derivatives thereof, acrylamide and derivatives thereof, zwitterionic compounds, water-soluble silane coupling agents, and water-soluble thiol compounds. Further specific examples thereof include, but are not limited to, ethyleneglycol oligomers, (N-isopropylacrylamide) oligomers, methacryloyloxyethylphosphorylcholine oligomers, low-molecular-weight dextran, low-molecular-weight heparin, oligoethyleneglycolthiol, ethylene glycol, diethylene glycol, triethylene glycol, tetraethylene glycol, 2-[methoxy (polyethyleneoxy)]propyltrimethoxysilane, and triethylene glycol-terminated thiol.

The average thickness of a hydrophilic membrane is preferably 0.8 nm to 500 μm, more preferably 0.8 nm to 100 μm, further preferably 1 nm 10 μm, and most preferably 1.5 nm to 1 μm. When the average thickness is 0.8 nm or more, protein adsorption and cell adhesion are unlikely to be influenced by regions on the substrate surface that have not been covered with a hydrophilic membrane, which is preferable. In addition, when the average thickness is 500 μm or less, coating is relatively easy.

Examples of a method for forming a hydrophilic membrane on a base substrate surface include: a method comprising allowing a base substrate to directly adsorb a hydrophilic organic compound; a method comprising directly coating a base substrate with a hydrophilic organic compound; a method comprising coating a base substrate with a hydrophilic organic compound, followed by cross-linking treatment; a method comprising forming a hydrophilic membrane on a base substrate in a multistep manner in order to increase the degree of adhesion therebetween; a method comprising forming a foundation layer on a base substrate and coating the foundation layer with a hydrophilic organic compound in order to increase the degree of adhesion therebetween; and a method comprising forming a polymerization initiation point on a substrate surface, followed by polymerization of a hydrophilic polymer brush.

Among the above membrane formation methods, particularly preferable methods are a method comprising forming a hydrophilic membrane on a base substrate in a multistep manner and a method comprising forming a foundation layer on a base substrate and coating the foundation layer with a hydrophilic organic compound in order to increase the degree of adhesion therebetween. With the use of such methods, the degree of adhesion between a hydrophilic organic compound and a base substrate can be readily increased. The term "bonding layer" is used herein. The term "bonding layer" refers to a layer located between the uppermost hydrophilic membrane layer and the substrate when a coating membrane comprising a hydrophilic organic compound is formed in the multistep manner. Also, it refers to a foundation layer when a foundation layer is formed on the base substrate surface and a hydrophilic membrane layer is formed on the foundation layer. Such bonding layer is preferably a layer comprising a material having bonding portions (linkers). Examples of a combination of a linker and a functional group located at the end of a material substance to be bound to the linker include: an epoxy group and a hydroxyl group; phthalic anhydride and a hydroxyl group; a carboxy group and N-hydroxysuccinimide; a carboxy group and carbodiimide; and an amino group and glutaraldehyde. In each combination, either one of the components may be a linker. In the above methods, prior to coating with a hydrophilic material, a bonding layer comprising a material having linkers is formed on a substrate. The density of the material in the bonding layer is an important factor based on which the bonding force is determined. The density can be simply evaluated with the use of a water contact angle on the bonding layer surface as an index. For instance, in the case of a silane coupling agent (epoxy silane) having an epoxy group on its end, the water contact angle on the substrate surface to which epoxy silane is added is typically 45° or more and desirably 47° or more. Accordingly, a substrate having sufficient cell adhesion inhibitory properties can be produced by adding an ethyleneglycol-based material to the substrate in the presence of an acid catalyst.

(Biodegradable Sheet)

A biodegradable sheet used for production of a contraction-inhibited cell sheet is not particularly limited as long as it has cell adhesion properties and strength to such an extent that the biodegradable sheet is not deformed due to contraction of a cell sheet; that is to say, sufficient strength to such an extent that the biodegradable sheet can withstand deformation caused by contraction of a cell sheet (which is referred to as "sufficient strength" in the present invention). Examples of a material for such biodegradable sheet include: polylactic acid; poly(lactic acid-butyric acid) copolymers; polybutyric acid; polyglycol acid; collagens and crosslinked collagens; gelatins and crosslinked gelatins; and artificial polypeptides and crosslinked artificial polypeptides.

(Method for Producing a Cell Culture Carrier)

A method for producing a cell culture carrier according to the present invention is not particularly limited. However, a cell culture carrier can be produced in the following manner. The surface of the above base substrate is coated with a solution used for forming the above organic thin film. Next, a support is provided to the coat of the solution. Then, the coat with the support is allowed to gel, for example, such that a step of forming the organic thin film is completed.

(Cell)

Cells to be cultured with the use of the cell culture carrier of the present invention may be floating cells such as hematopoietic cells and lymphoid cells or adhesive cells. However, the cell culture carrier of the present invention is preferably used for adhesive cells. Examples of such cells include: hepatocytes, which are hepatic parenchymal cells, and Kupffer cells; endothelial cells such as vascular endothelial cells and corneal endothelial cells; fibroblasts; osteoblasts; osteoclasts; periodontal membrane-derived cells; epidermal cells such as epidermal keratinocytes; epithelial cells such as tracheal epithelial cells, digestive tract epithelial cells, cervical epithelial cells, and corneal epithelial cells; mammary gland cells; pericytes; myocytes such as smooth muscle cells and cardiomyocytes; renal cells; Langerhans cells in the pancreas; neurons such as peripheral neurons and optic neurons; chondrocytes; and osteocytes. Such cells may be primary cells collected from a tissue or an organ. Alternatively, cells obtained via subculture of such cells over several generations may be used. Further, the above cells may be embryonic stem cells, which are undifferentiated cells, pluripotent stem cells such as mesenchymal stem cells having pluripotency, unipotent stem cells such as vascular endothelial progenitor cells having unipotency, or differentiated cells. In addition, for cell culture, a single cell line may be cultured. Alternatively, at least two cell lines may be cocultured.

(Culture)

A sheet-type cell layer can be formed by causing cell culture on a cell culture carrier, on which the above cells have been seeded, in a culture solution. Any culture solution can be used without particular limitation as long as it is a cell culture medium that is generally used in the art. Examples of a cell culture medium that can be used depending on cell type include basal media (e.g., basal media described in "Tissue Culture Technique edited by The Japanese Tissue Culture Association (third edition)" published by Asakura Publishing Co., Ltd., p. 581) such as an MEM medium, a BME medium, a DME medium, an αMEM medium, an IMDM medium, an ES medium, a DM-160 medium, a Fisher medium, an F12 medium, a WE medium, and an RPMI1640 medium. Further, a serum (e.g., fetal bovine serum), a variety of proliferation factors, an antibiotic, an amino acid, and the like may be added to a basal medium. In addition, a commercially available serum-free medium such as a Gibco serum-free medium (Invitrogen) can be used. In view of clinical application of a cell tissue obtained as a final product, it is preferable to use a medium not containing animal-derived components.

The present invention is hereafter described in greater detail with reference to the following examples, although the technical scope of the present invention is not limited thereto.

EXAMPLE 1

Collection of a Support-Held Cell Sheet 1-1. Production of a Base Substrate Having a Static Water Contact Angle of 45° or Less and Cell Adhesion Inhibitory Properties Toluene (39.0 g) and TSL8350 (GE Toshiba Silicone Co., Ltd.) (0.8 g) were mixed together and triethylamine (450 µl) was added thereto during agitation. The resultant was continuously agitated at room temperature for several minutes and the full volume thereof was transferred to a glass dish. A 10-cm square glass substrate subjected to UV cleaning was immersed therein and left at room temperature for 16 hours. Thereafter, the glass substrate was washed with ethanol and water, followed by drying with nitrogen blowing. Next, concentrated sulfuric acid (25 µl) was added dropwise to tetraethyleneglycol (TEG) (50 g) during agitation. The resultant was continuously agitated for several minutes and the full volume thereof was transferred to a glass dish. The above substrate was immersed therein, followed by reaction at 80° C. for 20 minutes. After reaction, the substrate was sufficiently washed with water, followed by drying with nitrogen blowing. Accordingly, a coating membrane comprising TEG was formed on the glass substrate surface. The static water contact angle of the surface was approximately 30°. The substrate was cut in a size of 25 mm×15 mm and an obtained piece was used as a base substrate having a static water contact angle of 45° or less and cell adhesion inhibitory properties. The base substrate was subjected to autoclave sterilization. Then, an MEM medium containing 5% fetal bovine serum was added in an adequate amount thereto. Bovine aorta endothelial cells ($2.0 \times 10^5$ cells for a single base substrate) were seeded thereon, followed by culture in an incubator (37° C., 5% $CO_2$) for 24 hours. As a result, it was found that no cells adhered to the base substrate surface.

1-2. Production of a Collagen Thin Film and Measurement of the Film Thickness

As a support, a polyethyleneterephthalate film (thickness: 16 µm; external size: 25 mm×15 mm; internal size: 20 mm×9 mm; Teijin DuPont film) was used. A collagen solution was adjusted to have a final concentration of 2.4 mg/ml on ice with the use of a collagen gel culture kit (Cellmatrix I-A, Nitta Gelatin Inc.). A portion of the solution (40 µl) was added with the support to the base substrate produced in 1-1. The solution was allowed to gel at 37° C. for 1 hour, followed by drying in a clean bench for 3 hours. Thus, a collagen thin film was produced. The thickness of the collagen thin film was measured with a sensing-pin-type surface profilometer (Dektak FPD-650, Nihon Shinku Gijutsu K.K.). As a result, the thickness was found to be 770±191 nm. It was found that the thus produced collagen thin film adhered to the base substrate even after addition of PBS for hydration.

1-3. Collection of a Support-Held Cell Sheet

Figure 6:
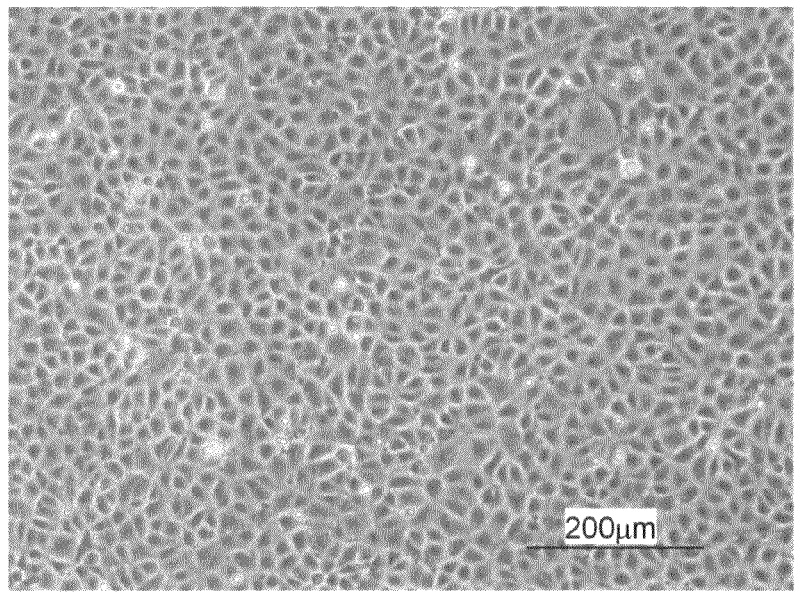
FIG. 6 is a phase-contrast microscopic image of a support-held cell sheet comprising bovine aorta endothelial cells.
Figure 7:
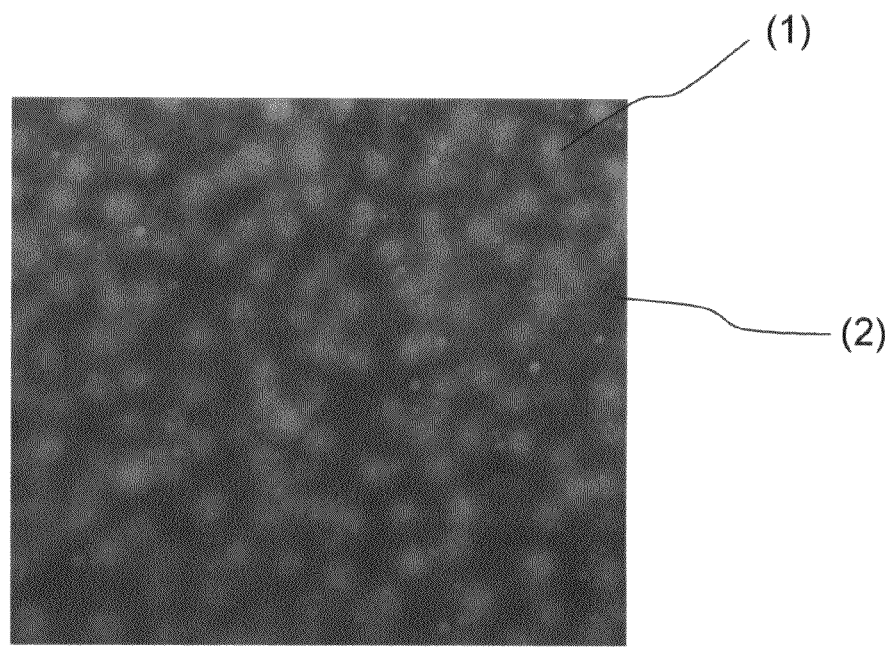
FIG. 7 is a confocal microscopic image of a support-held cell sheet comprising bovine aorta endothelial cells.

An MEM medium containing 5% fetal bovine serum was added in an adequate amount to the collagen thin film produced in 1-2. Bovine aorta endothelial cells ($2.0 \times 10^5$ cells for a single base substrate) were seeded thereon, followed by culture in an incubator for 24 hours. Cell adhesion and proliferation took place on the collagen thin film such that confluent cells were obtained. Thereafter, the support was held with a pair of tweezers for detachment such that the support-held cell sheet supported on the collagen thin film was removed from the base substrate and collected. The thus produced support-held cell sheet was observed with a phase-contrast microscope (IX71, Olympus) (FIG. 6). As a result, the support-held cell sheet did not experience cell contraction and the shape thereof was maintained, allowing handling thereof with the support. The collagen thin film was subjected to immunostaining (primary antibody: rabbit anti type I collagen; secondary antibody: alexa fluor 488 goat anti rabbit), and cell nuclei were stained with Hoechst. The results of double staining were observed with a confocal microscope (Axiovert 200M, zeiss) (FIG. 7). As a result, the produced cell layer was found to be supported by the collagen thin film.

EXAMPLE 2

Comparative Example Regarding the Collagen Content Per Unit Area of Base Substrate and the Type of Base Substrate The collagen content per unit area of base substrate was changed from 5 to 150 µg/cm². In addition, a base substrate comprising polystyrene (cell culture dish; FALCON), a base substrate comprising glass, and a base substrate subjected to chemical treatment by the method used in 1-1 in Example 1 were compared with each other. Except for the above, Example 2 was carried out as in the case of Example 1. Distinction between defective products and qualified products was made based on the following point: whether the majority of cells remained on the base substrate after damage to the collagen thin film caused by removal of the support-held cell sheet from the base substrate; or a cell sheet formed with the majority of cells was obtained without damage to the collagen thin film. Tables 1 and 2 list the relationships between defective products and qualified products. The static water contact angles of the base substrates used in the experiments (the polystyrene base substrate, the glass base substrate, and the base substrate subjected to chemical treatment by the method use in 1-1 in Example 1) were 51°, approximately 0° (almost not detectable), and 30°, respectively.

TABLE 1

| Collagen content [µg/cm²] | 13 | 27 | 53 | 67 | 80 | 107 | 133 |
|---|---|---|---|---|---|---|---|
| Polystyrene | X | X | X | X | X | X | ◯ |
| Glass | X | ◯ | ◯ | ◯ | ◯ | ◯ | ◯ |

◯: Qualified product;
X: Defective product

TABLE 2

| Collagen content [µg/cm²] | 7 | 10 | 13 | 17 | 20 | 23 |
|---|---|---|---|---|---|---|
| Glass | X | X | X | X | X | X |
| Base substrate chemically treated by the method 1-1 | X | ◯ | ◯ | ◯ | ◯ | ◯ |

◯: Qualified product;
X: Defective product

EXAMPLE 3

Lamination of Support-Held Cell Sheets

Figure 8:
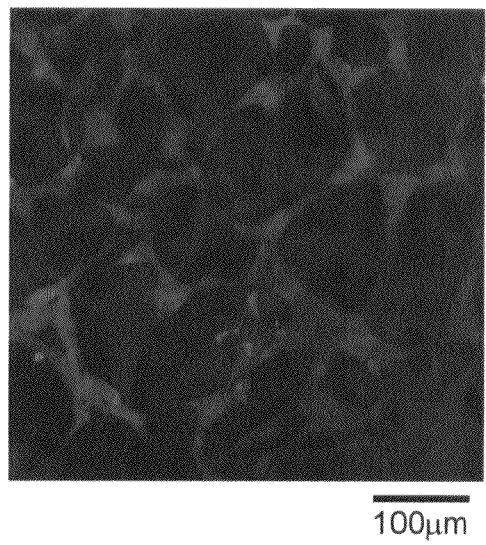
FIG. 8 is a confocal microscopic image of a calcein-stained laminate of support-held cell sheets comprising bovine aorta endothelial cells.
Figure 9:
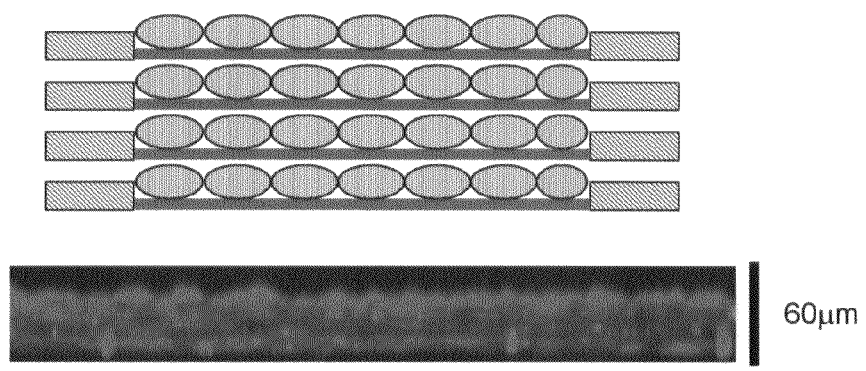
FIG. 9 shows confocal microscopic observation results for a calcein-stained laminate of support-held cell sheets comprising bovine aorta endothelial cells (the bottom of FIG. 9) and a cross-sectional schematic view of the laminate (the top of FIG. 9).

On the support-held cell sheet produced in Example 1, a support-held cell sheet produced in the same manner was laminated in a manner such that a collagen thin film came into contact with cells. The medium was suctioned such that the support-held cell sheet was slightly immersed in the medium. Thus, the support-held cell sheets came into contact with each other via surface tension. After 4 hours for lamination, a medium was newly added thereto such that the obtained multilayer support-held cell sheet was sufficiently immersed in the medium. The above support-held cell sheets were found to adhere to each other so that both sheets were moved together when one of the support-held cell sheets was moved. Similar operations were repeated to laminate 4 layers, followed by culture for 2 days. Then, cells were stained with calcein and observed with a confocal microscope (FIG. 8). As a result, bovine aorta endothelial cells were found to form a network. In addition, as a result of cross-sectional confocal microscopic observation (FIG. 9), a collagen thin film with a thickness much less than the cell thickness was present between each two cell layers. Accordingly, there was a non-fluorescent stained region with a very low degree of thickness between each two cell layers.

EXAMPLE 4

Figure 10:
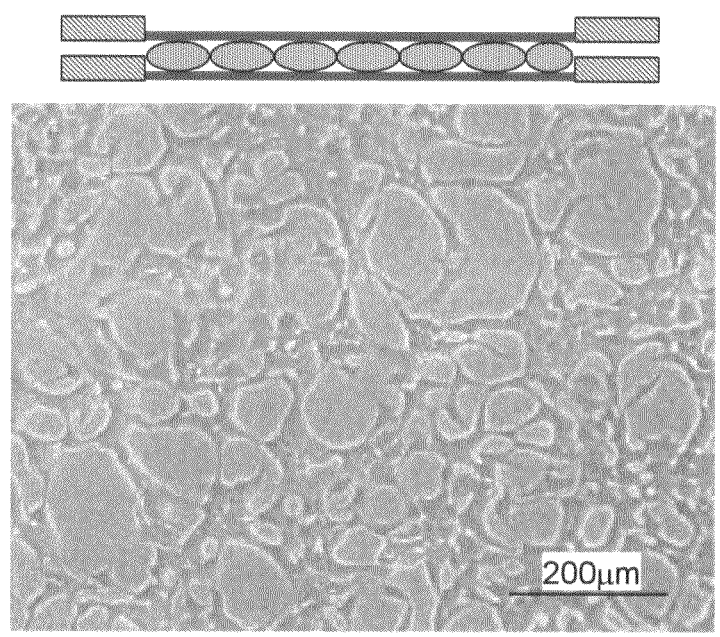
FIG. 10 shows a phase-contrast microscopic image of a 2-day-cultured laminate obtained by laminating a support-held culture membrane on a support-held cell sheet comprising bovine aorta endothelial cells (the bottom of FIG. 10) and a cross-sectional schematic view of the laminate (the top of FIG. 10).

Collection of a Support-Held Culture Membrane Followed by Lamination of the Support-Held Culture Membrane on a Single Layer Support-Held Cell Sheet An MEM medium containing 5% fetal bovine serum was added in an adequate amount to a cell culture carrier comprising a collagen thin film produced as in Example 1 (1-1 and 1-2), followed by hydration. Then, the support was held with a pair of tweezers for detachment such that the support-held culture membrane (collagen thin film) was removed from the base substrate and collected. The obtained support-held culture membrane was laminated on a support-held cell sheet produced as in Example 1, followed by culture for 2 days. Accordingly, an organic thin film-covered support-held cell sheet was formed, followed by observation with a phase-contrast microscope (FIG. 10). As a result, bovine aorta endothelial cells were found to form a network.

EXAMPLE 5

Collection and Lamination of Fibroblast Cell Sheets

Figure 11:
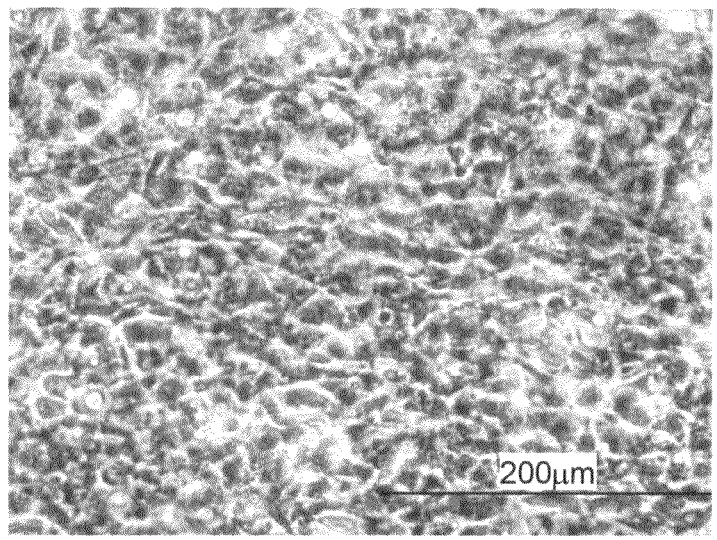
FIG. 11 is a phase-contrast microscopic image of a laminate of support-held cell sheets comprising fibroblasts.

A DMEM medium containing 10% fetal bovine serum was added in an adequate amount to a cell culture carrier comprising a collagen thin film produced as in Example 1 (1-1 and 1-2). Mouse fibroblasts ($2.0 \times 10^5$ cells for a single base substrate) were seeded thereon, followed by culture in an incubator for 24 hours. Cell adhesion and proliferation took place on the collagen thin film such that confluent cells were obtained. It was possible to remove and collect the support-held cell sheet from the base substrate in the same manner as in 1-3 of Example 1. The support-held cell sheet did not experience cell contraction, allowing handling thereof with the support. Support-held cell sheets were laminated to form 3 layers in the same manner as in Example 3, followed by culture for 2 days. As a result of observation with a phase-contrast microscope (FIG. 11), cell layers were found to adhere to each other and formation of a network, which was observed in the case of bovine aorta endothelial cells, was not observed.

EXAMPLE 6

Figure 12:
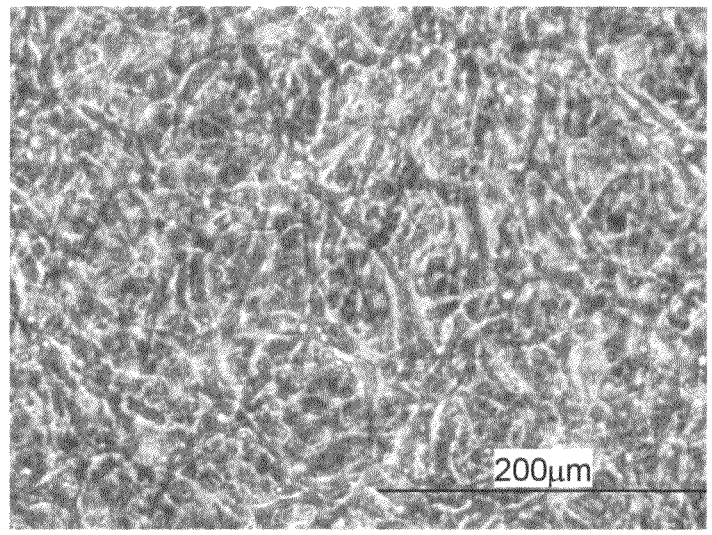
FIG. 12 shows phase-contrast microscopic observation results for a 3-day-cultured laminate obtained via co-lamination of a support-held cell sheet of vascular endothelial cells and a support-held cell sheet of fibroblasts.

Co-Lamination of a Sheet of Vascular Endothelial Cells and a Sheet of Fibroblasts A mouse fibroblast support-held cell sheet produced as in Example 5 was allowed to overlap on a support-held cell sheet comprising bovine aorta endothelial cells produced as in Example 1 in a manner such that cells adhered to a collagen thin film. The medium was completely suctioned and then a DMEM medium containing 10% fetal bovine serum was newly added thereto such that the support-held cell sheet was slightly immersed in the medium, followed by lamination in the same manner as in Example 3. Further, a support-held cell sheet comprising bovine aorta endothelial cells produced as in Example 1 was further laminated thereon for co-lamination of the support-held cell sheets comprising vascular endothelial cells and fibroblasts, followed by culture for 3 days. As a result of observation with a phase-contrast microscope (FIG. 12), the cell layers were found to adhere to each other.

EXAMPLE 7

Separation of a Support from a Cell Sheet

A collagen sheet having a certain strength (thickness: 30 µm; Nippi, Inc.) was laminated on the support-held cell sheet laminated (2 layers) in Example 3 in the same manner as in Example 4. Then, the support was separated using an ultrasonic cutter. As a result, the cell sheet did not experience cell contraction.

EXAMPLE 8

Figure 13:
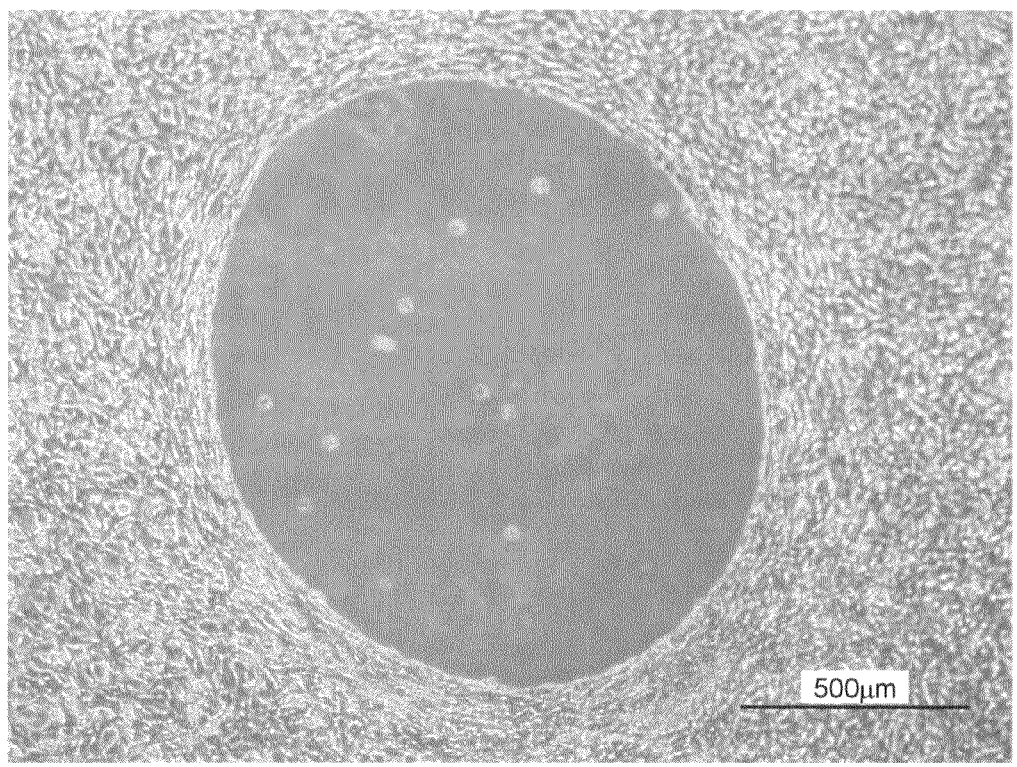
FIG. 13 shows observation results for a patterned support-held cell sheet.

A Patterned Support-Held Cell Sheet Comprising a Patterned Collagen Thin Film Collagenase was added to a portion of a cell culture carrier comprising a collagen thin film produced as in Example 1. Collagen contained in the portion was degraded, resulting in detachment of the degraded collagen from the base substrate. Thus, a cell culture carrier comprising the thus patterned collagen thin film was produced. Bovine aorta endothelial cells ($2.0 \times 10^5$ cells for a single base substrate) were seeded thereon, followed by culture for 24 hours. Accordingly, cells did not adhere to the portion from which collagen had been detached while cells exclusively adhered to the portion on which the collagen thin film remained. The support was held with a pair of tweezers for detachment such that the patterned support-held cell sheet was removed from the base substrate and collected (FIG. 13).

EXAMPLE 9

Collection of a Support-Held Cell Sheet 9-1. Production of a Base Substrate Having a Static Water Contact Angle of 45° or Less and Cell Adhesion Inhibitory Properties Toluene (39.0 g) and TSL8350 (GE Toshiba Silicone Co., Ltd.) (0.8 g) were mixed together and triethylamine (450 µl) was added thereto during agitation. The resultant was continuously agitated at room temperature for several minutes and the full volume thereof was transferred to a glass dish. A 10-cm square glass substrate subjected to UV cleaning was immersed therein and left at room temperature for 16 hours. Thereafter, the glass substrate was washed with ethanol and water, followed by drying with nitrogen blowing. Next, concentrated sulfuric acid (25 µl) was added dropwise to tetraethyleneglycol (TEG) (50 g) during agitation. The resultant was continuously agitated for several minutes and the full volume thereof was transferred to a glass dish. The above substrate was immersed therein, followed by reaction at 80° C. for 20 minutes. After reaction, the substrate was sufficiently washed with water, followed by drying with nitrogen blowing. Accordingly, a coating membrane comprising TEG was formed on the glass substrate surface. The static water contact angle of the surface was approximately 30°. The substrate was cut in a size of 25 mm×15 mm and an obtained piece was used as a base substrate having a static water contact angle of 45° or less and cell adhesion inhibitory properties. The base substrate was subjected to autoclave sterilization. Then, an MEM medium containing 5% fetal bovine serum was added in an adequate amount thereto. Bovine aorta endothelial cells ($2.0 \times 10^5$ cells for a single base substrate) were seeded thereon, followed by culture in an incubator (37° C., 5% $CO_2$) for 24 hours. As a result, it was found that no cells adhered to the base substrate surface.

9-2. Production of a Collagen Thin Film and Measurement of the Film Thickness

As a support, a polyethyleneterephthalate film (thickness: 16 μm; external size: 25 mm×15 mm; internal size: 20 mm×9 mm; Teijin DuPont film) was used. A collagen solution was adjusted to have a final concentration of 1.2 mg/ml by adjusting the pH of an atelocollagen (acid collagen solution I-PC; Koken Co., Ltd.), which is a nonantigenic collagen, to neutral with the use of Hepes buffer and $NaHCO_3$. A portion of the solution (20 μl) was added with the support to the base substrate produced in 9-1. The solution was allowed to gel at 37° C. for 4 hours, followed by drying in a clean bench for 3 hours for UV crosslinking. Thus, a collagen thin film was produced. The thickness of the collagen thin film was measured with a sensing-pin-type surface profilometer (Dektak FPD-650, Nihon Shinku Gijutsu K.K.). As a result, the thickness was found to be 103±9 nm. It was found that the thus produced collagen thin film adhered to the base substrate even after addition of PBS for hydration.

9-3. Collection of a Support-Held Cell Sheet

An MEM medium containing 5% fetal bovine serum was added to the collagen thin film produced in 9-2. Bovine aorta endothelial cells ($2.0 \times 10^5$ cells for a single base substrate) were seeded thereon, followed by culture in an incubator for 24 hours. Cell adhesion and proliferation took place on the collagen thin film such that confluent cells were obtained. Thereafter, the support was held with a pair of tweezers for detachment such that the support-held cell sheet supported on the collagen thin film was removed from the base substrate and collected. The thus produced support-held cell sheet was observed with a phase-contrast microscope (IX71, Olympus). As a result, the support-held cell sheet did not experience cell contraction and the shape thereof was maintained, allowing handling thereof with the support.

EXAMPLE 10

Comparison Aregarding the Collagen Content Per Unit Area of Base Substrate

The collagen content per unit area of base substrate was changed from 4 to 23 μg/cm². Except for the above, Example 10 was carried out as in the case of Example 9. Distinction between defective products and qualified products was made based on the following point: whether the majority of cells remained on the base substrate after damage to the collagen thin film caused by removal of the support-held cell sheet from the base substrate; or a cell sheet formed with the majority of cells was obtained without damage to the collagen thin film. Tables 1 and 3 list the relationships between defective products and qualified products.

TABLE 3

| Collagen content [μg/cm²] | 4 | 6 | 7 | 10 | 13 | 17 | 20 | 23 |
|---|---|---|---|---|---|---|---|---|
| | X | ○ | ○ | ○ | ○ | ○ | ○ | ○ |

EXAMPLE 11

Lamination of Support-Held Cell Sheets

On the support-held cell sheet produced in Example 9, a support-held cell sheet produced in the same manner was laminated in a manner such that a collagen thin film came into contact with cells. The medium was suctioned such that the support-held cell sheet was slightly immersed in the medium. Thus, the support-held cell sheets came into contact with each other via surface tension. After 4 hours for lamination, a medium was newly added thereto such that the obtained multilayer support-held cell sheet was sufficiently immersed in the medium. The above support-held cell sheets were found to adhere to each other so that both sheets were moved together when one of the support-held cell sheets was moved.

EXAMPLE 12

Collection and Lamination of Fibroblast Cell Sheets

A DMEM medium containing 10% fetal bovine serum was added in an adequate amount to a cell culture carrier comprising a collagen thin film produced as in Example 1 (9-1 and 9-2). Mouse fibroblasts ($2.0 \times 10^5$ cells for a single base substrate) were seeded thereon, followed by culture in an incubator for 24 hours. Cell adhesion and proliferation took place on the collagen thin film such that confluent cells were obtained. It was possible to remove and collect the support-held cell sheet from the base substrate in the same manner as in 9-3 of Example 9. The support-held cell sheet did not experience cell contraction, allowing handling thereof with the support.

INDUSTRIAL APPLICABILITY

According to the present invention, a cell sheet that can be readily detached from a cell culture carrier and is inhibited from contracting after being detached is provided. Changes in the degree of binding between cells and the base substrate do not cause detachment of a cell sheet in the present invention. Therefore, the present invention is applicable to any cell species. In addition, when an organic thin film is subjected to patterning according to need for the cell culture carrier of the present invention, it becomes possible to readily control cell distribution. In such case, a thick tissue can be formed. Further, in the case of the cell sheet comprising an organic thin film and a cell layer that is obtained in the present invention, an organic thin film layer portion can be formed that is thinner than that obtained by the technique disclosed in Patent Document 7 or 8. Therefore, in the present invention, a network can be readily formed between cell sheets that have overlapped each other upon lamination. Further, it can be expected that inter-cell layer paracrine interaction can be obtained.

All publications, patents, and patent applications cited herein are incorporated herein by reference in their entirety.

The invention claimed is:

1. A cell culture carrier, which comprises: (1) a support-held culture membrane comprising an organic thin film having cell adhesion properties and biodegradability, and a frame-like support fixed on the periphery of the organic thin film for maintaining the dimensions of the organic thin film; and (2) a base substrate having a surface with a static water contact angle of 45° or less, wherein the organic thin film within the support-held culture membrane is in contact with the surface of the base substrate and is detachable from the base substrate.

2. The cell culture carrier according to claim 1, wherein the surface of the base substrate has cell adhesion inhibitory properties.

3. The cell culture carrier according to claim 1, wherein the organic thin film is a biologically-derived material.

4. The cell culture carrier according to claim 1, wherein the organic thin film is formed with an artificially synthesized biomimetic material.

5. The cell culture carrier according to claim 1, wherein the dry weight per unit area of the organic thin film is 5 to 100 µg/cm².

6. The cell culture carrier according to claim 1, wherein the organic thin film is subjected to patterning.

7. The cell culture carrier according to claim 1, wherein the frame-like support has a thickness of 1 µm to 20 µm.

8. The cell culture carrier according to claim 1, wherein the organic thin film is formed with collagen.

9. The cell culture carrier according to claim 1, wherein the frame-like support is fixed to the organic thin film only at lateral surfaces of the organic thin film.

10. A method for producing a support-held cell sheet, comprising culturing cells on the organic thin film of the cell culture carrier according to claim 1 so as to form a sheet-type cell layer and detaching the cell layer with the support-held culture membrane from the base substrate, thereby obtaining a support-held cell sheet comprising the support-held culture membrane and the cell layer.

* * * * *